(12) United States Patent
Thompson

(10) Patent No.: US 6,537,262 B2
(45) Date of Patent: Mar. 25, 2003

(54) FEMALE URINE COLLECTOR

(76) Inventor: Garey Thompson, P.O. Box 731, Dayton, NJ (US) 08810

( * ) Notice: Subject to any disclaimer, the term of this patent is extended or adjusted under 35 U.S.C. 154(b) by 0 days.

(21) Appl. No.: 09/878,959

(22) Filed: Jun. 13, 2001

(65) Prior Publication Data

US 2002/0193760 A1 Dec. 19, 2002

(51) Int. Cl.[7] .................. A61M 1/00; A61F 5/44; A47K 11/00
(52) U.S. Cl. .......... 604/347; 604/326; 604/327; 604/329; 604/331; 604/335; 4/144.2; 4/144.3
(58) Field of Search .................. 604/326, 327, 604/329, 331, 335, 347; 4/144.2, 144.3

(56) References Cited

U.S. PATENT DOCUMENTS

| | | | | |
|---|---|---|---|---|
| 901,134 A | * | 10/1908 | Weidl | 4/144.3 |
| 3,680,543 A | * | 8/1972 | Cox | 4/144.1 |
| 4,121,306 A | * | 10/1978 | Bringman et al. | 4/144.3 |
| 4,681,572 A | * | 7/1987 | Tokarz et al. | 600/574 |
| 4,815,477 A | * | 3/1989 | McWhorter et al. | 251/4 |
| 5,370,637 A | * | 12/1994 | Brodeur | 4/144.3 |
| 5,605,161 A | * | 2/1997 | Cross | 4/144.2 |

* cited by examiner

Primary Examiner—William C. Doerrler
Assistant Examiner—Filip Zec
(74) Attorney, Agent, or Firm—Barbara R. Greenberg

(57) ABSTRACT

An upright female urine collector having a horizontally accordion pleated rectangular shaped urine collection receptacle with a tube outlet, the tube housing a manually operated two way valve disposed to direct urine flow either to a sample reservoir containing a chemical reagent test strip or to a urine sample collector. The two way valve can be spring activated or can be hand turned for instant urine flow redirection. In an alternate embodiment, an upright female urine collector has a urine collection receptacle modified to retain the chemical reagent test strip in a trench with exit means for quick test results observation.

6 Claims, 3 Drawing Sheets

FEMALE URINE COLLECTOR

BACKGROUND OF THE INVENTION

This invention relates to a female urine collector, more particularly a collapsible female urine collector for upright urine collection that can be directed to a container provided with medical test strips, to a collection reservoir or to a toilet.

DESCRIPTION OF THE PRIOR ART

Female urine collection devices to provide urine for urine analysis are well known in the prior art. Urine analysis is a quick, non-invasive and inexpensive way to assess the health of an individual. However, the female anatomy presents unique challenges to the collection of a urine sample. In the female urination process, an emerging stream is not visible to a urinator. In order to direct a urine stream into a container, prevent urine splashing and overflowing, prevent contamination of the urine and other unpleasant urine collection mishaps, a variety of urine collector configurations and outlet systems have been developed.

U.S. Pat. No. 5,605,161 discloses an upright urinary collection device comprising a collapsible funnel shaped body with positioning loops used to place the device against the user's body. Chemical test strips are secured to the collector's interior surface. This device has two obvious inadequacies. The funnel shape does not correspond to female anatomy and urine flow pressure directly on test strips can entirely erode embedded chemicals and even wash away an entire strip.

U.S. Pat. Nos. 5,370,637 and 4,681,572 illustrate upright urine collection devices that are flexible and collapse. Neither separate a urine sample for test paper analysis and midstream collection.

U.S. Pat. No. 4,121,306 provides a conical shaped cylindrical urinal for bedfast patients with valve means to direct urine flow to a reservoir or to a sample bottle. A quick release valve mechanism for easy user urine flow diversion is not disclosed nor are means for chemical test strip analysis described.

SUMMARY OF THE INVENTION

The present invention provides a novel upright female urine collector not anticipated, suggested or rendered obvious by any urine collectors now present in the prior art.

A principle objective of the present invention is to provide an upright female urine collector to be used for controlled, clean, uncontaminated, reliable and safe physical health condition testing requiring chemical reagent test strip analysis.

Another objective is to provide a female urine collector that can be used without hand holding.

Another objective of the invention is to provide an upright urination means for females when toilet facilities are not available.

An additional object of the invention is to provide a female urine collector where urine flow can be rapidly guided by user valve flow operation.

Still another object of the invention is to provide a chemical reagent testing means where a test strip is not hand held.

Another object of the invention is to provide a means for a female user to observe and thereby control urine flow.

An additional object of the invention is to provide a means for performing a chemical reagent test and collecting a urine sample both at the same time.

Finally, another object of the invention is to provide an upright urination device that females can use to avoid strange toilet seat contact.

Other objectives, advantages and features will become apparent with reference to the drawings, specification and claims.

DETAILED DESCRIPTION OF THE INVENTION

Figure 1:
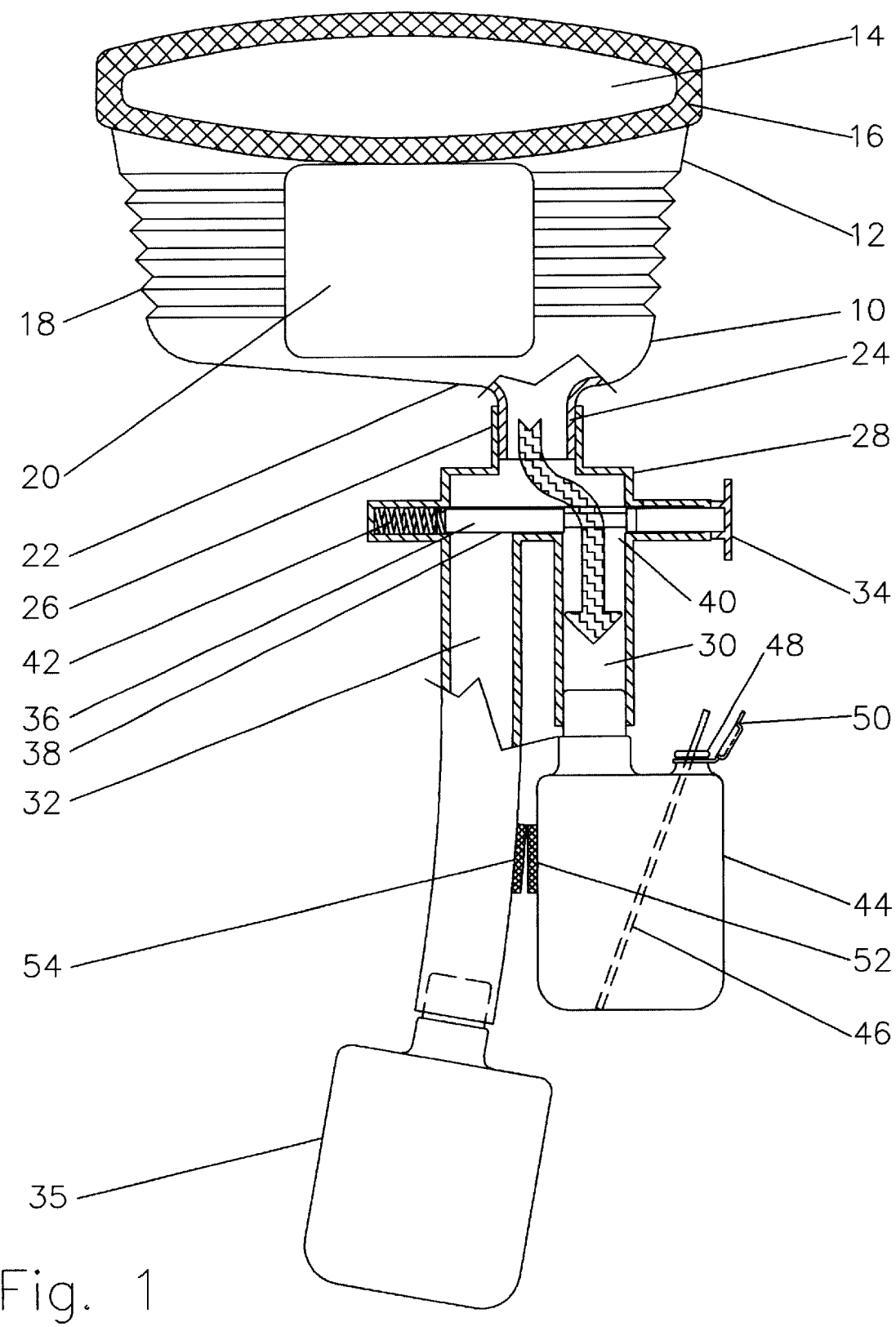
FIG. 1 is a perspective partially exposed side view of the female upright urine collector.

Referring now to the drawings and particularly to FIG. 1, a female upright urine collector 10 is shown having a urine collection receptacle 12 with a rectangular top opening 14 having rounded corners, the receptacle 12 top rim 16 fitted with a soft pliable substance such as a gel for comfortable, secure and easy positioning over a female genital region. In a preferred embodiment, the urine collection receptacle 12 is horizontally accordion pleated 18 to be used in an open position when urine is collected and in a collapsed position when stored or shipped. The receptacle 12 can be fitted on each side wall with a soft pad such as a gel pad 20. A user,can fit the open collection receptacle 12 soft pliable substance rim 16 to a similarly shaped female genital region and hold the receptacle 12 in place using friction force from inner thigh pressure against the gel pad 20. Hand holding is not necessary.

Emerging from the urine collection receptacle 12 floor 22 is a flexible tube 24, which can be one half inch in diameter, joined to tube 26 which is expanded to house a two way valve 28. Flexible tube 24 can be telescopically secured to tube 26 allowing a snug connection, easy removal and easy rotation so urine collection receptacle 12 and tube 26 can be turned and used in a direction convenient to the user. Urine flows from receptacle 12 through tubes 24, 26 to valve 28. Beyond valve 28 tube 26 is bifurcated into test reservoir conduit 30 and sample collector conduit 32. Referring to FIG. 1, two way valve 28 is manually operated by a user pressing valve button 34 to slide barrier 36 so as to snuggly seal sample collector conduit 32 outlet 38. Now urine flows through valve 28 into a test reservoir outlet 40 through test reservoir conduit 30. Pressing valve button 34 also compresses relaxed spring 42 and release of valve button 34 allows spring 42 decompression which urges barrier 36 back to its original resting position over test reservoir conduit 30 opening 40. Now valve 28 directs urine flow through outlet 38 into sample collector conduit 32. From sample collector conduit 32, urine can flow to an open receptacle such as a toilet bowl or to a standard urine sample collector 35 removably secured to urine sample collector conduit 32. Urine sample collector 35 can be telescopically and frictionally engaged to a tapered distal end of sample collector conduit 32. Sample collector conduit 32 can have a tapered distal end for a secure and easily removable connection to urine sample collector 35.

As shown by an arrow in FIG. 1, when a user diverts urine flow from the sample collector conduit 32 by pushing valve button 34 and allowing urine to flow to test reservoir 44, there the urine can strike a chemical reagent test strip 46. Chemical reagent test strip 46 is placed obliquely in test reservoir 44 to insure test strip 46 urine contact. Chemical reagent test strip 46, and tests strips generally, require small amounts of urine to show test results. A large urine flow can wash chemical indicator reagents from test strips negating test results. Manual user instant control of button 34 allows ideal urine amounts to impact test strips. Since initial urine samples can contain undesirable foreign substances, a user can select midstream urine for test purposes. Test strips can be used to test for pregnancy as well as urine pH, glucose, bilirubin and other health status indicators.

Test reservoir 44 has a shoulder opening 48 for chemical reagent test strip 46 extension and easy removal. A seal 50 for shoulder opening 48 prevents urine overflow. A Velcro® strip 52 anchored to a test reservoir 44 side wall can adhere to an oppositely disposed Velcro® strip 54 affixed to sample collector conduit 32 so urine weight cannot dislodge test reservoir 44 from test reservoir conduit 30. In addition, the stabilized test reservoir 44 is visible to a user who can instantly observe a chemical reagent test strip result such as a pregnancy test result without handling a test strip. Test reservoir conduit 30 can have a tapered distal end to telescopically and frictionally engage test reservoir 44 for a tight secure connection but also easy removal.

Figure 2:
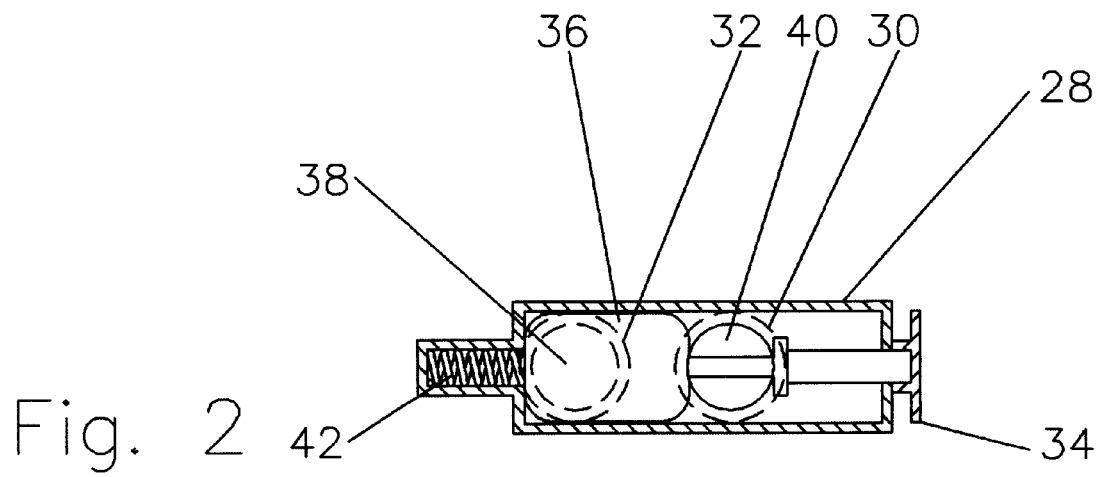
FIG. 2 is a top view of a two way valve directing urine flow to a chemical reagent strip container.

Referring to FIG. 2, a top view of two way valve 28 shows barrier 36 sealing sample collector conduit 32 outlet 38 to create a tight seal and divert a urine flow through outlet 40 to test reservoir conduit 30 and then into test reservoir 44 accomplished by pressure on button 34 that cooperates with spring 42. Button 34 release moves barrier 36 in a position to seal test reservoir conduit 30 outlet 40. To maintain a stable position, barrier 36 slides in a two way valve 28 interior wall groove.

Figure 3:
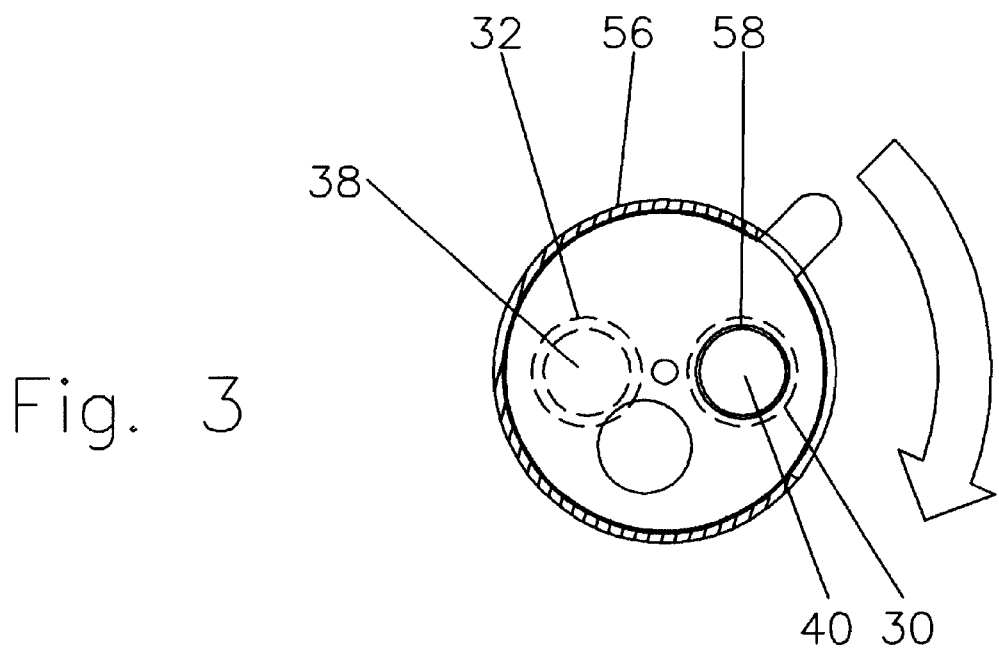
FIG. 3 is a top view of an alternate two way valve.

An alternative embodiment of the female urine collector 10 valve system is depicted in FIG. 3. Here a two way disc valve 56 comprising a flat circular disk with a circular opening 58 sized and located to correspond to test reservoir conduit 30 outlet 40 and sample collector conduit 32 outlet 38. Two way disc valve 56 is operated by hand turning means to move circular opening 58 directly over outlet 40 allowing urine to flow from receptacle 12 to flexible tube 24 through two way disc valve 56 circular opening 58 and outlet 40 into test reservoir conduit 30 and then test reservoir 44. When disc valve 56 is operated to open test reservoir conduit 30 then sample collector conduit 32 is sealed. Two way disc valve 56 can also instantly turn to move circular opening 58 directly over outlet 38 while sealing outlet 40 thus directing urine flow into a urine sample collector 35.

In addition to the female upright urine collector 10 features already described in detail, the following more fully describes the present invention. The urine collection receptacle 12 can have an inner surface flap to prevent urine back splashing. The receptacle 12 preferably opens to a length of five inches and collapses to a one half inch length. It can be constructed of a thin plastic material colored blue, pink and yellow along with other light spring colors. Also, it should be understood that a variety of two way valve systems such as a springless, slide operated valve can work in the present invention to direct urine flow.

In order to facilitate upright use of the female upright urine collector 10 and avoid hand holding, a saddle shaped gel pad can be wrapped around the urine collection receptacle 12 with a gel pad narrow portion covering the urine collection receptacle 12 floor exterior and wider portions covering the urine collection receptacle 12 exterior side walls for inner thigh friction force adhesion.

Figure 4:
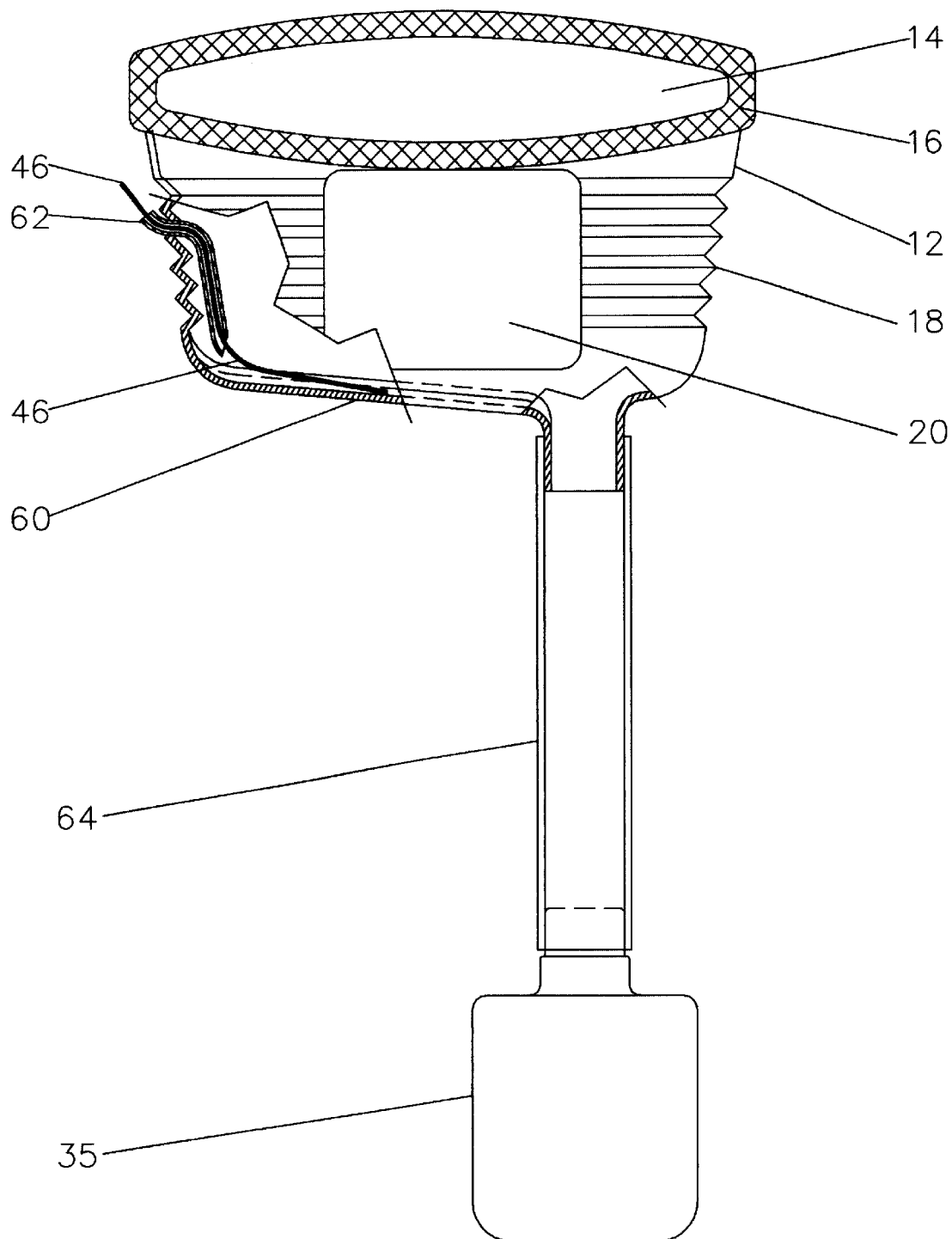
FIG. 4 is a partially exposed side view of another embodiment of the female upright urine collector.

FIG. 4 depicts a urine collection receptacle 12 modified to have a floor 22 trench 60 for chemical test reagent strip 46 retention, the strip 46 extending into a conduit 62, preferably made of a plastic material, disposed along the urine collection receptacle 12 inner front wall. The chemical reagent test strip 46 exits through a thin slot in the urine collection receptacle 12 front wall located about three fourths of the distance from the urine collection receptacle 12 floor 22 to the rim 16. The flexible tube 24 extending from the urine collection receptacle 12 floor 22 is removably secured to tube 26 housing either valve 28 as shown in FIG. 1 or two way disc valve 56 as shown in FIG. 3 bifurcating into test reservoir conduit 30 and sample collector conduit 32 and into test reservoir 44 and urine sample collector 34, respectively. Using this assembly, a user can perform two urine analysis tests, such as a pregnancy test and a glucose test, simultaneously.

In addition, the urine collection receptacle 12 modified to have a floor 22 trench 60 containing chemical reagent test strip 46 can exit urine through flexible tube 24 into a securably removable tube 64 that can conduct urine directly into a receptacle such as a toilet or to the removably secured urine sample collector 35. The chemical test reagent strip 46 can be a pregnancy detection strip for a user's quick observation of a pregnancy test result.

The foregoing description and drawings are intended to be illustrative examples only and all equivalent relationships to those described in the specification and illustrated in the drawings are intended to fall within the scope of the present invention. Further, since numerous changes and modifications including variations in size, materials, shape, function, form and manner of assembly, operation and use will readily occur to those skilled in the art, it is not desired to limit the present invention to the exact construction and operation shown and described hereto.

What is claimed is:

1. An upright female urine collector comprising
   a horizontally pleated urine collection receptacle having a rectangular top opening corresponding to a female genital region, a soft pliable substance adhered to a top opening rim and having soft side wall pads;
   a flexible tube emerging from a urine collection receptacle floor;
   a tube removably secured to said flexible tube and then expanded;
   a two way valve housed in said expanded tube, said two way valve having two outlets wherein button pressure compresses a spring that slidingly moves a barrier, said barrier disposed to slide in an expanded tube housing interior wall groove, from a sealing position over one of said outlets to seal said other outlet, button release reversing the process;
   a bifurcation of said expanded tube resulting in directing said outlets to a sample collector conduit and a test reservoir conduit removably secured to a urine sample collector and a test reservoir, respectively, said test reservoir having opening means for inserting a chemical reagent test strip and
   said upright female urine collector having said test reservoir affixed to said sample collector conduit by Velcro® means.

2. The upright female urine collector of claim 1 wherein a saddle shaped gel pad covers said urine collector receptacle, a narrow portion of said saddle shaped gel pad covering said urine collector receptacle exterior floor and said saddle shaped gel pad wider portions covering said urine collector receptacle exterior side walls.

3. An upright female urine collector comprising a horizontally pleated urine collection receptacle having a rectangular top opening corresponding to a female genital region, a soft pliable substance adhered to a top opening rim and having soft side wall pads;

a flexible tube emerging from a urine collection receptacle floor;

a tube removably secured to said flexible tube and then expanded;

a two way valve housed in said expanded tube, said two way valve having two outlets wherein button pressure compresses a spring that slidingly moves a barrier, said barrier disposed to slide in an expanded tube housing interior wall groove, from a sealing position over one of said outlets to seal said other outlet, button release reversing the process;

a bifurcation of said expanded tube resulting in directing said outlets to a sample collector conduit and a test reservoir conduit removably secured to a urine sample collector and a test reservoir, respectively, said test reservoir having opening means for inserting a chemical reagent test strip and said upright female urine collector having said test reservoir affixed to said sample collector conduit by Velcro® means.

4. The upright female urine collector of claim 3 wherein a saddle shaped gel pad covers said urine collector receptacle, a narrow portion of said saddle shaped gel pad covering said urine collector receptacle exterior floor and said saddle shaped gel pad wider portions covering said urine collector receptacle exterior side walls.

5. An upright female urine collector comprising a horizontally pleated urine collection receptacle having a rectangular top opening corresponding to a female genital region, a soft pliable substance adhered to a top opening rim and having soft side wall pads, said urine collection receptacle having a floor trench for chemical reagent test strip retention, said chemical reagent test strip emerging through a conduit disposed along an inner front wall of said urine collection receptacle that provides a pathway for said chemical reagent test strip exit through said inner front wall;

a flexible tube emerging from a urine collection receptacle floor;

a tube removably secured to said flexible tube and then expanded;

a two way valve housed in said expanded tube, said two way valve having two outlets wherein button pressure compresses a spring that slidingly moves a barrier, said barrier disposed to slide in an expanded tube housing interior wall groove from a sealing position over one of said outlets to seal said other outlet, button release reversing the process;

a bifurcation of said expanded tube resulting in directing said outlets to a sample collector conduit and a test reservoir conduit removably secured to a urine sample collector and a test reservoir, respectively, said test reservoir having opening means for inserting a second chemical reagent test strip and said upright female urine collector having said test reservoir affixed to said sample collector conduit by Velcro® means.

6. An upright female urine collector comprising a horizontally pleated urine collection receptacle having a rectangular top opening corresponding to a female genital region, a soft pliable substance adhered to a top opening rim and having soft side wall pads, said urine collection receptacle having a floor trench for chemical reagent test strip retention, said chemical reagent test strip emerging through a conduit disposed along an inner front wall of said urine collection receptacle that provides a pathway for said chemical reagent test strip exit through said inner front wall;

a flexible tube emerging from a urine collection receptacle floor;

a tube removably secured to said flexible tube and then expanded;

a two way valve housed in said expanded tube, said two way valve having two outlets wherein button pressure compresses a spring that slidingly moves a barrier, said barrier disposed to slide in an expanded tube housing interior wall groove from a sealing position over one of said outlets to seal said other outlet, button release reversing the process;

a bifurcation of said expanded tube resulting in directing said outlets to a sample collector conduit and a test reservoir conduit removably secured to a urine sample collector and a test reservoir, respectively, said test reservoir having opening means for inserting a second chemical reagent test strip and said upright female urine collector having said test reservoir, in addition, affixed to said sample collector conduit by Velcro® means.

* * * * *